United States Patent
Harjunmaa et al.

(10) Patent No.: US 10,139,340 B2
(45) Date of Patent: Nov. 27, 2018

(54) NONINVASIVE REFRACTOMETER

(71) Applicants: Hannu Harjunmaa, Holden, MA (US); Sinikka Harjunmaa, Holden, MA (US)

(72) Inventors: Hannu Harjunmaa, Holden, MA (US); Sinikka Harjunmaa, Holden, MA (US)

( * ) Notice: Subject to any disclaimer, the term of this patent is extended or adjusted under 35 U.S.C. 154(b) by 0 days.

(21) Appl. No.: 15/195,346

(22) Filed: Jun. 28, 2016

(65) Prior Publication Data
US 2017/0115214 A1 Apr. 27, 2017

Related U.S. Application Data

(60) Provisional application No. 62/246,032, filed on Oct. 24, 2015, provisional application No. 62/186,301, filed on Jun. 29, 2015.

(51) Int. Cl.
| | |
|---|---|
| *G01N 21/41* | (2006.01) |
| *C12G 1/00* | (2006.01) |
| *G01B 11/06* | (2006.01) |
| *G01N 33/14* | (2006.01) |

(52) U.S. Cl.
CPC ........... *G01N 21/4133* (2013.01); *C12G 1/00* (2013.01); *G01B 11/06* (2013.01); *G01B 11/0633* (2013.01); *G01N 21/41* (2013.01); *G01N 33/143* (2013.01); *G01N 33/146* (2013.01); *G01N 33/14* (2013.01); *G01N 2201/06113* (2013.01)

(58) Field of Classification Search
CPC ............ G01N 21/4133; G01N 33/143; G01N 33/146; G01N 2201/06113
USPC ................... 356/128, 364, 446, 440
See application file for complete search history.

(56) References Cited

U.S. PATENT DOCUMENTS

| | | | | |
|---|---|---|---|---|
| 5,396,325 A | * | 3/1995 | Carome | G01N 21/552 356/128 |
| 6,419,342 B1 | * | 7/2002 | Bronswijk | B41J 2/2135 347/19 |
| 7,652,767 B2 | * | 1/2010 | Harsh | G01J 3/02 356/445 |
| 9,354,168 B2 | * | 5/2016 | Sartorius | G01N 21/3577 |
| 2003/0095248 A1 | * | 5/2003 | Frot | G01N 21/431 356/128 |
| 2004/0130706 A1 | * | 7/2004 | Frot | G01N 21/43 356/128 |
| 2010/0231911 A1 | * | 9/2010 | Fischer | G01J 4/02 356/364 |

* cited by examiner

*Primary Examiner* — Isiaka Akanbi
(74) *Attorney, Agent, or Firm* — Gerry A. Blodgett; David J. Blodgett; Blodgett & Blodgett, P.C.

(57) ABSTRACT

The present invention pertains to the measurement of the refractive index of a medium, such as a fluid, through the wall of its container. The essential characteristic of the invention is that, by using at least two separate light paths that are of unequal length and that reflect from the wall/medium interface, it is possible to perform the measurement of the refractive index of the medium so that the result is insensitive to the color and thickness of the wall.

6 Claims, 4 Drawing Sheets

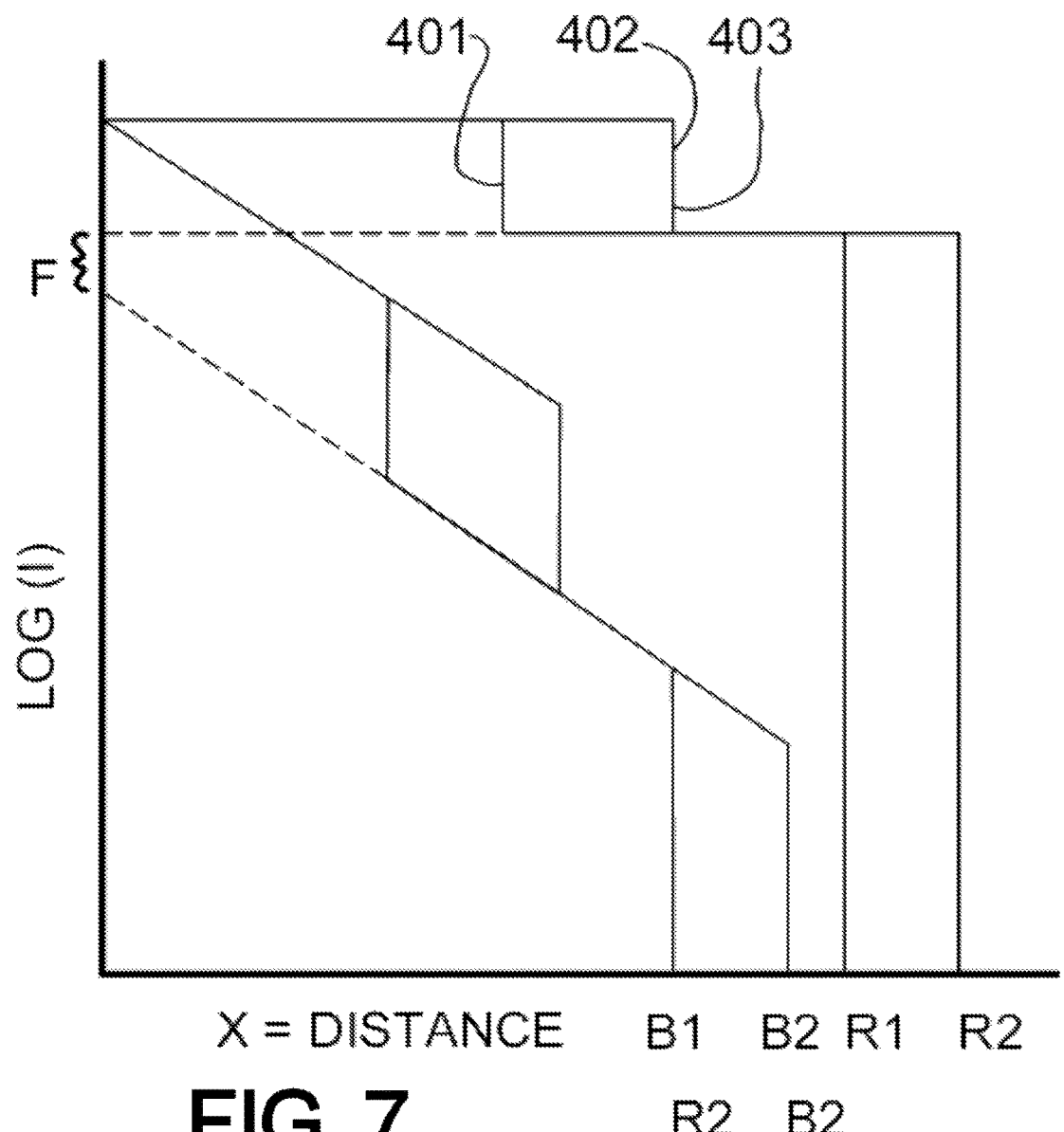

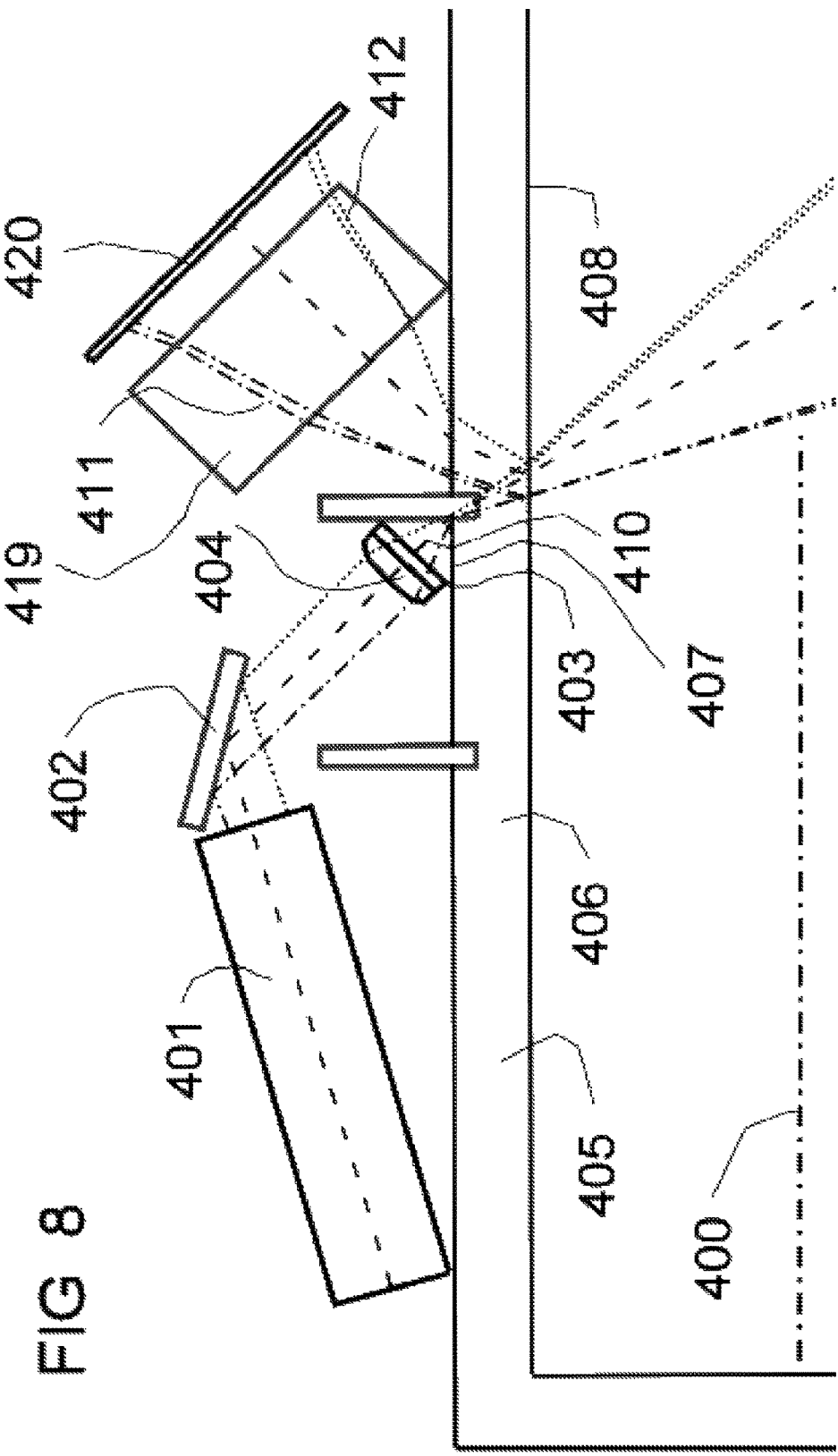

NONINVASIVE REFRACTOMETER

CROSS-REFERENCE TO RELATED APPLICATIONS

This application claims the benefit under 35 U.S.C. 119(e) of both U.S. Provisional Application No. 62/186,301 filed Jun. 29, 2015 and U.S. Provisional Application No. 62/246,032 filed Oct. 24, 2015 which are both hereby incorporated by reference.

STATEMENT REGARDING FEDERALLY SPONSORED RESEARCH OR DEVELOPMENT

This invention has been created without the sponsorship or funding of any federally sponsored research or development program.

FIELD OF THE INVENTION

The present invention pertains to the measurement of the refractive index of a medium, such as a fluid, through the wall of its container

BACKGROUND OF THE INVENTION

There are many situations where the refractive index of a fluid needs to be measured, for instance in commercial, industrial or medical applications. A conventional refractometer requires a sample of the fluid to be taken out of its container. This patent application describes a method that does not require a sample to be taken: the fluid may remain in its container, which may remain closed. The exemplary application in the description is to measure the sugar content of wine in an unopened bottle.

It is of interest to know the sugar content of wines, however, the degree of sweetness often is not indicated on the bottle label, and, if it is indicated, it is usually in most general terms, such as "semi-dry" or "extra dry". Some wine-producing regions, such as Germany and Austria as well as the Alsace region in France, bottle many different degrees of sweetness of wines otherwise similar in packaging, which causes confusion with consumers, and at worst, poor food-wine pairings and uneasy dinners.

In another instance, a bottle of counterfeit wine can be discerned by measuring the sugar content of the wine.

In yet another instance, a wine merchant needs to be able to recommend wines for her customers with precision with regards to the sugar content.

Also, in yet another instance, diabetic persons need to know the sugar content of a beverage that they are considering.

These and other difficulties experienced with the prior art products and methods have been obviated in a novel manner by the present invention.

It is therefore, an outstanding object of some embodiments of the present invention to provide a means for ascertaining the true sugar content of a bottled wine without opening the bottle.

Another object of some embodiments of the present invention is to decrease the resulting confusion caused by vague sugar content labeling on some wine bottles.

A further object of some embodiments of the present invention is to improve the ability of a consumer to match up the sugar content of a particular wine with compatible foods.

A still further object of some embodiments of the present invention is to decrease the possibility of a host serving a wine which has an inappropriate sugar level at a particular dinner event where such a characteristic of the wine is important.

A still further object of some embodiments of the present invention is to uncover an unexpected sugar content of a bottled wine which may suggest that the bottled wine is a counterfeit.

A still further object of some embodiments of the present invention is to supplement the ability of a wine merchant to recommend wines for her customers with precision with regards to the sugar content.

A still further object of some embodiments of the present invention is to assist a diabetic in recognizing if a particular bottle of wine has an appropriate sugar content level for their particular health needs.

With these and other objects in view, as will be apparent to those skilled in the art, the invention resides in the combination of parts set forth in the specification and covered by the claims appended hereto, it being understood that changes in the precise embodiment of the invention herein disclosed may be made within the scope of what is claimed without departing from the spirit of the invention.

BRIEF SUMMARY OF THE INVENTION

The present invention pertains to the measurement of the refractive index of a medium, such as a fluid, through the wall of its container. The essential characteristic of the invention is that, by using at least two separate light paths that are of unequal length and that reflect from the wall/medium interface, it is possible to perform the measurement of the refractive index of the medium so that the result is insensitive to the color and thickness of the wall, and insensitive to the color of the fluid.

BRIEF DESCRIPTION OF THE SEVERAL VIEWS OF THE DRAWINGS

FIG. 7 shows a graph depicting the light intensity as a function of travel in the glass.

FIG. 8 shows a schematic representation of an alternative embodiment using an array detector.

DETAILED DESCRIPTION OF THE INVENTION

It has been found that the refractive index of a liquid can be measured by taking a sample of it and placing the sample in a refractometer. Several versions of refractometers have existed for a long time. As a rule, they measure the refractive index by showing the critical angle of total internal reflection between the sample and a glass (or sapphire etc.) prism. The angle is read visually on a scale, or by photodetectors.

The method of the present invention does not measure the critical angle. Instead, it measures the so-called Fresnel reflection that occurs at the interface on the container wall and its contents. The Fresnel reflection depends on the difference of the refractive indices on the two sides of the interface. This allows the measurement of the index of liquids enclosed in unopened containers, such as wine in wine bottles. Although most wine is fermented dry, there is an important market segment of sweet and semi-sweet wines and liqueurs. The relation between the refractive index and the soluble solids (sugar) content is known; therefore, from the Fresnel reflection, first the index and then the sugar content can be calculated.

Although the following embodiment describes the measurement of sugar content in wine, it is obvious that the method can be applied to many solutions in containers or pipes, such as gelatin, etc.

One characteristic of the invention is that, by using at least two separate light paths that are of unequal length and that reflect from the wall/medium interface, it is possible to perform the measurement of the refractive index of the medium so that the result is insensitive to the color and thickness of the wall.

There are many ways to define the light paths. For example, lenses and apertures can be used. Alternatively, an overfilled detector may serve to define the light path, wherein, only the light that reaches the detector is detected. It is noted that, in every case, in order to properly measure the Fresnel reflection, it is necessary that the reflection from the first (outer) wall surface of the glass container be prevented from reaching the detector.

Figure 3:
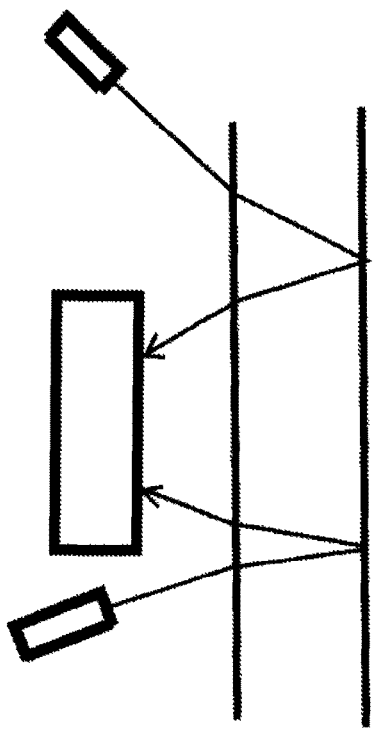
FIG. 3 shows a configuration with two narrow-beam light sources and one large-area detector.
Figure 4:
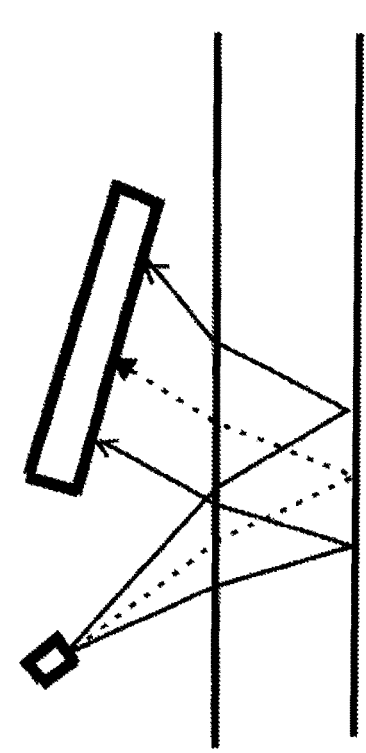
FIG. 4 shows a configuration with one fan-beam light source and a linear array detector.
Figure 5:
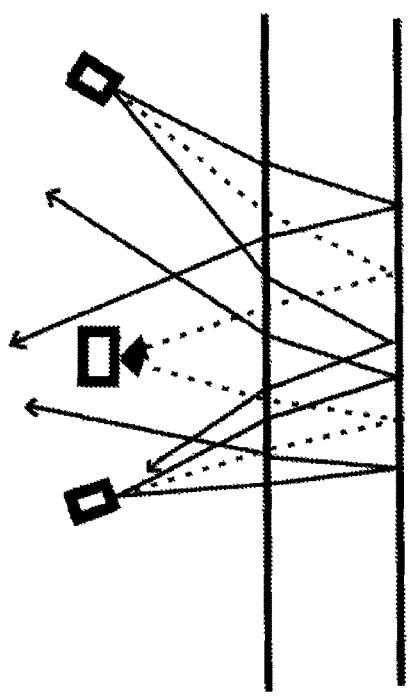
FIG. 5 shows a configuration with two fan-beam light sources and one small detector.
Figure 6:
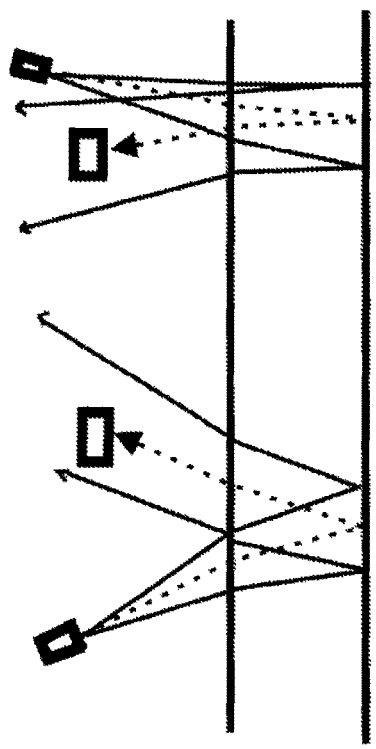
FIG. 6 shows a configuration with two independent combinations of a fan-beam light source and a small detector.

Different incident angles are used to provide a plurality of different pathlengths in the glass. This allows the algorithm to compensate for absorption of light in different-colored glasses. It is to be noted that the plurality of beams can be achieved either by using more than one light source or more than one detector, or an array detector. FIGS. 2,3,4, and 5 show several alternative configurations that achieve two paths of different lengths. FIG. 3 shows a configuration with two narrow-beam light sources and one large-area detector. The light sources can be on opposite sides or on the same side from the detector. FIG. 4 shows a configuration with one fan-beam light source and a linear array detector. FIG. 5 shows a configuration with two fan-beam light sources and one small detector. The light sources can be on opposite sides or on the same side from the detector. FIG. 6 shows a configuration with two independent combinations of a fan-beam light source and a small detector. In all configurations, the light sources and detectors are in one plane, to avoid the effects of the curvature of the cylindrical bottle wall.

Figure 1:
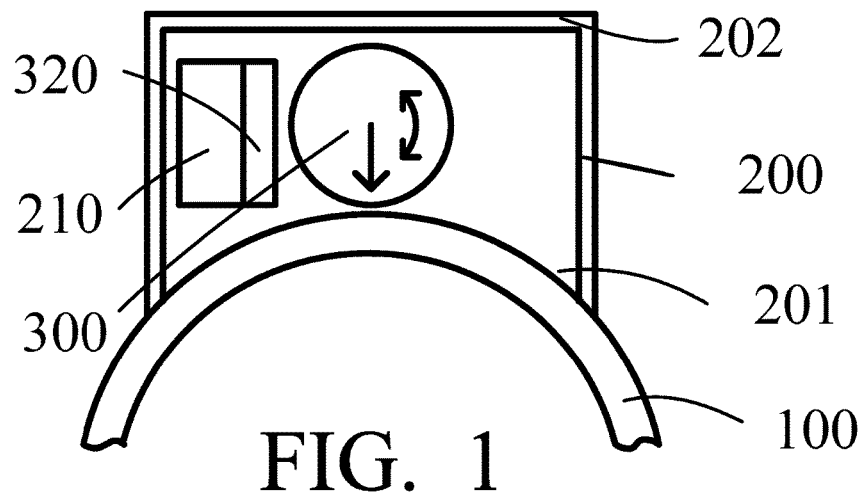
FIG. 1 shows a schematic representation of the device.
Figure 2:
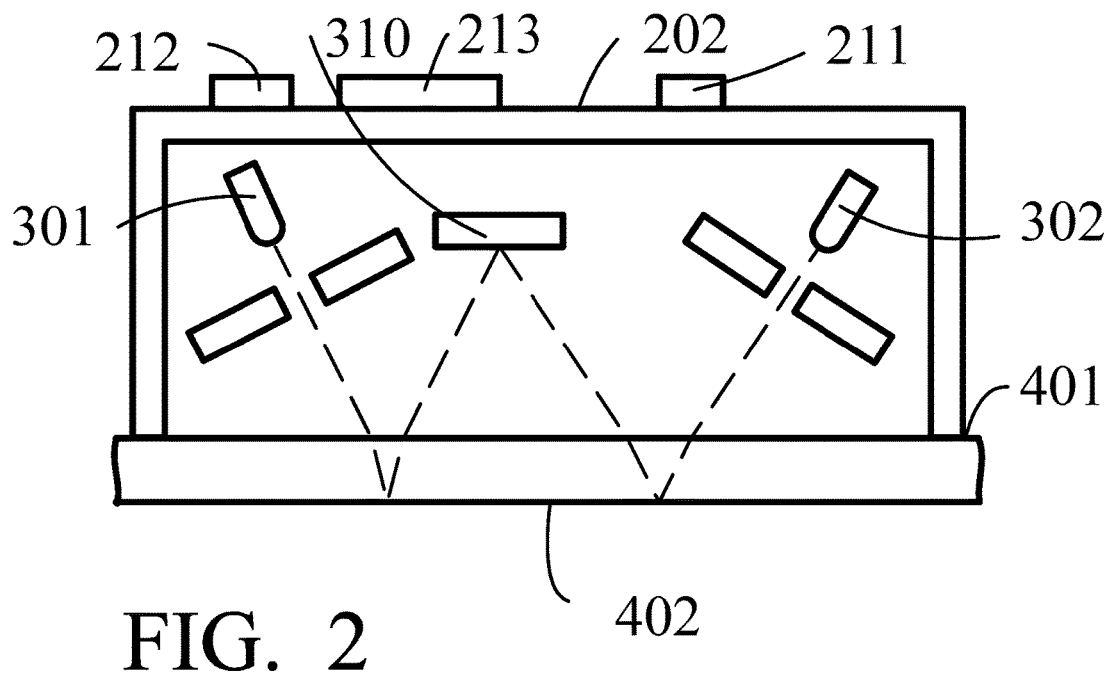
FIG. 2 shows a schematic representation of an alternative optical configuration of the device.

Now, as shown in FIGS. 1 and 2, as an example for the purposes of this description, the medium whose refractive index is to be measured is assumed to be in a glass bottle 100. It will be obvious for a person skilled in the art how the method can be applied for other kinds of samples and containers. The measurement result using this method is insensitive to the color and thickness of the bottle wall, within certain reasonable limits.

The device according to the method is a hand-held box 200, with an optical sensor surface 201 which is pressed against the side of the bottle, and a user interface surface 202 on the opposing side. Surface 202 contains input means, such as pushbuttons 211 or dial 212. It also contains a display 213.

The optical sensor surface 201 has light conduits that guide the light from a plurality of (in this example, two) light sources 301, 302 into the bottle wall with different incident angles. Both Fresnel reflections from the glass/liquid interface 402 reach a large-area photodetector 310. Total internal reflection never occurs at interface 402. The reflection from the glass/air interface 401 is prevented from reaching the detector. When the device is in contact with the bottle, all light paths are in one plane that contains the axis of the bottle, and the device is in a vertical orientation against the side of the bottle.

Control unit 210 causes the light sources to alternate between the OFF and ON states so that only one of them is ON at any time. The frequency of alternation is, for instance, 100 Hz.

The incident angles are designed to ensure that both beams fall on the detector active area when the wall thickness varies within a predetermined range that encompasses all standard glass beverage bottles.

Due to the two above properties of the system, the measurement result is independent of bottle color and wall thickness.

PREFERRED EMBODIMENT

In a preferred variation, where the reference plate is part of the device, the optical system is mounted on a rotatable module 300 inside the box 200.

FIG. 1 shows the device in contact with the bottle, looking along the axis of rotation of the optical module. FIG. 2 shows the device from the side.

The rotation is typically 90 degrees around an axis parallel to the bottle axis. As a result of the rotation, the optical system makes contact with a clear glass reference plate 320 located inside box 200, in the same way as it does with the bottle. When performing a measurement, the signals are recorded from the distal surface of the reference plate and the bottle separately. The readings from the reference plate are used to normalize the bottle readings. The transition between reference-plate measurement and bottle measurement can be arranged in other ways besides rotation, such as translation (sliding) in a way easily established by those skilled in the art.

Light is attenuated as it propagates in glass according to the Beer-Lambert law:

$$I = I_0 \exp(-kx)$$

where
  I=attenuated intensity
  $I_0$=original intensity
  k=absorption coefficient
  x=distance traveled.

The product kx can be called optical thickness. Since k and x appear only together as a product and never separately, it does not matter which one changes when kx changes. The compensations for thickness and absorption are tied together.

The optional reference plate is made of clear glass and has negligible absorption at the wavelength of the light sources. Therefore, the Fresnel signals measured from the reference plate represent the losses due to the geometry which are the same for reference plate and bottle. If the bottle is colorless, the same signals should be obtained from an empty bottle. If the bottle is not empty, the Fresnel reflection signal is weaker, but it should retain the same ratio between the two light sources. If there is absorption, the ratio is changed. From the two bottle Fresnel reflection signals, the absorption-compensated signal can be obtained by extrapolation to zero absorption. That signal can then be compared to the reference-plate signal to obtain the bottle Fresnel reflection. A look-up table can be used to find the sugar content.

A detailed description of the thickness/absorption compensation follows, using the embodiment with two light sources and one detector as an example for simplicity. The same principle applies to other configurations, such as the array detector configuration described later. FIG. 7 shows a graph having x as the horizontal axis and log(I) as the vertical axis (a semi-log graph), the intensity is represented by a straight line pointing to the lower right (FIG. 7). The stronger the absorption in the glass, the steeper the angle. Light travelling on the two paths of different lengths 401 and 402, follows the same line, but the shorter path ends at a smaller value of x, before the longer path. The step down at the midpoint 403 represents the Fresnel reflection at the glass/liquid interface, where most of the light continues into the bottle, but the line continues to follow the reflected beam. Note that the line does not represent the direction of the light, but only the log of its intensity as a function of distance traveled in the glass. The ratio of the distances traveled in glass in the two pathlengths remains constant independent of the thickness of the bottle wall, and the angle of the line remains constant.

$$R=(L_2/(L_2-L_1))=\text{constant independent of thickness}$$

where
$L_1$=shorter length in glass
$L_2$=longer length in glass
In FIG. 3, Bi=Li for bottle, and Ri=Li for reference plate or calibrator, and i=1 or 2.

The straight line in the semilog graph representing the intensity in the glass can therefore be reconstructed by fitting a straight line through the two points that represent detected intensities, without knowledge of the wall thickness. By following the reconstructed line to zero x-coordinate, where the light enters the glass, the virtual original intensity, with the loss by the Fresnel reflection included, without absorbance will be recovered. If there are more than two detectors, a fitting procedure such as least-squares fit can be used.

$$\log(\text{Corrected intensity})=\log(I_2)+R*(\log(I_1)-\log(I_2))$$

where
$I_1$=measured intensity of the shorter path
$I_2$=measured intensity of the longer path Because of the long leverage arm of the extrapolation, the absorption correction may add noise and can be omitted when the absorption is low. When the absorption correction is performed, it is advisable to integrate several readings of each signal to average out the noise.

With the absorption-corrected intensities, the change in the Fresnel reflection F from reference plate to bottle can be deduced. From the Fresnel reflection, the refractive index can be deduced.

From the refractive index of the medium, some aspects of its composition can be deduced. For instance, if the medium is wine, its sugar content can be calculated, if its alcohol content is known. By law, the alcohol content is displayed on the label. Its percentage value can then be entered to the device before the measurement, using the pushbuttons 211 on the interface surface 202. A dial 212 can also be used in place of the pushbuttons. The algorithm can then use a formula or a look-up table to correct the result for the alcohol content.

The result of the calculation is displayed on display 213 (as shown in FIG. 1b). The unit of the sugar content can be either Brix (for practical purposes, percentage by mass) or g/l. The method can be used for clear media. If the medium is cloudy, or scatters light, the scattered light will be inseparable from the Fresnel reflection and will cause severe inaccuracy of the result.

Ambient light may reach the detector. Its effect is compensated for by measuring it while the light sources are shut off.

The great majority of beverage bottles are colorless or green. The laser light used in this invention should normally be a shade of green in order to minimize absorption in the glass and maximize the strength of the transmitted light. Therefore, a suitable wavelength is 525 nm (aqua green), where many bright light emitting diodes (LED) and diode lasers (LD) are available. Other shades of green may also be effective. The choice of the laser color/light frequency/wave length depends on a number of factors. In the case of bottles of a color other than the standard clear or green, lasers producing light of that other color may be effective.

The embodiment in the present example has a calibrator or reference plate built into the device. It is also possible to use an external calibrator, such as a water-filled bottle, to calibrate the device. This must be done frequently enough to avoid the effects of batteries losing charge, LED's aging etc.

The sugar content of wine is generally measured in one of two units, Brix (=%) or grams/liter (g/l). 10 g/l=1 Brix. Adding sugar to liquids makes their refractive index go up. The device according to this invention is a non-invasive refractometer that measures the refractive index of a liquid across a glass wall. In wine and juices, it is the sugar content that affects the index most. Alcohol affects the index as well, but since the alcohol content is always indicated on the label, its effect can be taken into account.

The measurement is based on the intensity of the Fresnel reflection. Cloudy liquids cannot be measured, because the back-scatter from the cloudiness interferes with the measurement. The color of the bottle does not have an effect on the result, because the absorption of light in the glass, if any, is compensated for by the multiple-beam optics according to this invention. The wall thickness of the bottle also has no effect on the result, due to the design of the optics according to this invention.

ALTERNATIVE EMBODIMENT USING AN ARRAY DETECTOR. FIG. 8 is a depiction of this embodiment. The axis of the bottle is marked as 400. The device uses a green laser light source 401 with an elliptical beam output. Coming out of the laser, the beam is deflected by beam splitter 402 and directed on a cylindrical lens 403 that forms a fan 410 out of the flat beam. As the device sits on the bottle 405 to be measured, the light paths are in a plane that is perpendicular to the bottle surface and parallel to the bottle axis. This way, the curvature of the bottle wall 406 has a minimal effect. The light fan enters the glass wall with its narrowest waist approximately at the air/glass interface 407 and with a central angle of 45 degrees. After travelling through the glass, the light meets the glass/liquid interface 408. There most of the light continues into the liquid, but a small fraction experiences a so-called Fresnel reflection and continues in the glass, now outward according to the law of reflection.

The Fresnel reflection happens at every interface where there is a change in the refractive index. It depends only on the difference of the refractive indices at the interface; it does not depend on other optical properties of the medium after the interface. That is why the measurement works for any color of wine or juice.

When the Fresnel-reflected light meets the glass/air interface 407 again, it is again split, most of it continuing in the air, refracted into the same angle it had when it entered the glass. The light fan then meets a cylindrical lens 419 that focuses the light and ensures that no light is lost due to the curvature of the bottle. Finally, the Fresnel-reflected ray fan 410 reaches a 16-element silicon linear array detector 420. The linear array detector 420 may have as many elements as is practical; for example, 256 elements. All of the fan energy is contained within the photosensitive area of the array. The total energy tells us the refractive index of the liquid in the bottle: the weaker the signal, the higher the refractive index and the higher the sugar content. The baseline signal is kept in memory from a calibration measurement on a bottle that contains dry wine or water.

Since the measurement is an intensity measurement, the possible absorption of light in the glass has to be compensated for. Most bottles are colorless or green and do not need this compensation. But should the glass happen to absorb light, a compensation mechanism is set up as follows: the light paths of the fan (defined by the detector element the light finally hits) travel unequal lengths in glass: those with the steepest entry angle 411 travel the shortest path and those with the shallowest entry angle 412 travel the longest path. The middle 12 elements of the array detector 420 are used to detect absorption by performing a least-squares fit on their signals: the slope of the fit, if different from that of the calibration, indicates the presence of absorption. It is then compensated for using a proprietary algorithm.—In order to eliminate the effects of ambient light, the measurement light is modulated (switched on and off at a rapid rate).

In another embodiment there is a flat portion 404 ground and polished in the center of the convex surface of the cylinderical lens 403. This flat allows the central portion of the flat beam to continue unrefracted, forming a central directional intensity peak. This intensity peak falls on the array detector 420 in a location determined by the thickness of the bottle wall 406. Thus, the thickness of the bottle wall is directly measured. The width of the flat portion on the cylinder lens preferably equals the element pitch of the array detector, in order to provide the best thickness resolution.

The first array detector element 421 has a special function: it is a reference detector. The beam splitter 402 transmits a small portion of the laser light 413 that then falls on the above-mentioned detector element. The signal thereby produced is used by the algorithm to normalize the array signals, thus making them independent of the actual laser intensity, which may depend on the aging of the laser, charge state of the battery etc. The last array detector element 422 also has a special function: baffle 423 causes it to look into the fluid without receiving any reflections from any interfaces. If the fluid is clear, it will see no light and will generate no signal. If the fluid is cloudy, some of the scattered light reaches this detector element, and a warning can then be issued. If there is too much scattered light reaching the middle of the array detector, the measurement is invalid.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desire to secure by Letters Patent is:

1. A non-invasive method of measuring the sugar content of a wine contained in a hermetically sealed transparent bottle, the method consisting of the following steps:
    (a) Shining at least two light sources through the bottle wall,
    each having a unique incident angle and Unique path length,
    (b) Measuring the intensity of the Fresnel reflection from each light source,
    (c) using the measured intensities of the fresnel reflections, in conjunction with the known alcohol content of the wine in order to calculate the sugar content of the wine contained within the bottle.

2. An apparatus for non-invasively measuring the sugar content of a wine contained in a hermetically sealed transparent bottle consisting of
    a hand-held box having:
        (a) an optical sensor surface on one side, which surface is in contact with the bottle,
            (i) on which light conduits are present, which guide light along paths in one plane,
                Which plane is congruent with the axis of the bottle, and which light paths enter into the bottle wall at unique incident angles,
                from a plurality of light sources, and
            (ii) which guided light produce Fresnel reflections at the glass/liquid interface,
                which Fresnel reflected light is, in turn, detected by a large-area photodetector,
        (b) a user interface surface on the opposing side having an input means for controlling and calibrating the apparatus, and a display;
        (c) a data base expressing the relationship of the index of refraction of the medium to the concentration of sugar in the wine; and
        (d) a comparator that compares a measured index of refraction to the data base;
    wherein the apparatus is arranged to measure the index of refraction of the wine, and by comparing the measured index of refraction of the wine to the data base is able to determine the concentration of the sugar in the wine.

3. The apparatus from claim 2, wherein a reference plate, made of clear glass and having a negligible absorption at the wavelength of the light sources, is part of the device and the optical system is mounted on a rotatable module inside the box, which rotatable module when rotated 90 degrees comes into contact with the reference plate and a measurement of the light readings from the reference plate are used to normalize the bottle readings.

4. The apparatus from claim 3, wherein the optical system is mounted in a translation sliding manner.

5. An apparatus for non-invasively measuring the sugar content of a wine contained in a hermetically sealed transparent bottle consisting of a hand-held box having:
    (a) a green laser light source with an elliptical beam output,
    (b) an aperture through which the elliptical beam is passed, further flattening and directing the beam on a cylindrical lens which causes a fan out of the flat beam,
    (c) the light path in a plane that is perpendicular to the bottle surface and parallel to the bottle axis,
    (d) the light fan entering the glass bottle wall with its narrowest waist approximately at the air/glass interface and with a central angle of 45 degrees,
    (e) a Fresnel reflection being created at the glass/wine interface,
    (f) the Fresnel reflection portion of the ray fan reaching a linear array detector situated outside the bottle,
    (g) an algorithm combining the measured intensities of the Fresnel reflections, in conjunction with the known alcohol content of the wine in order to calculate the sugar content of the wine contained within the bottle.

6. An apparatus as in claim 5, wherein
(a) the cylindrical lens includes a flat portion ground and polished in the center of the convex surface of the cylindrical lens, allowing the central portion of the flat beam to continue unrefracted, forming a central directional intensity peak,
(b) the central directional peak falling on the array detector in a location determined by the thickness of the bottle wall and therefore provided information about the thickness of the bottle wall.

* * * * *